(12) United States Patent
Kawahara et al.

(10) Patent No.: US 8,734,672 B2
(45) Date of Patent: May 27, 2014

(54) ICE CRYSTALLIZATION INHIBITOR DERIVED FROM BASIDIOMYCETE

(75) Inventors: Hidehisa Kawahara, Suita (JP); Yoshihide Koide, Nagano (JP); Naoki Arai, Takasago (JP); Jun Tomono, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 0 days.

(21) Appl. No.: 13/818,637

(22) PCT Filed: Aug. 11, 2011

(86) PCT No.: PCT/JP2011/068364
§ 371 (c)(1),
(2), (4) Date: Feb. 22, 2013

(87) PCT Pub. No.: WO2012/026339
PCT Pub. Date: Mar. 1, 2012

(65) Prior Publication Data
US 2013/0146803 A1 Jun. 13, 2013

(30) Foreign Application Priority Data
Aug. 25, 2010 (JP) .................. 2010-188436

(51) Int. Cl.
C09K 3/18 (2006.01)
C08K 3/00 (2006.01)
A23L 1/03 (2006.01)
A23L 1/30 (2006.01)
A01N 1/02 (2006.01)
A61K 8/73 (2006.01)
A61K 8/99 (2006.01)

(52) U.S. Cl.
USPC ................. 252/70; 252/71; 424/195.15

(58) Field of Classification Search
USPC .................... 252/70, 71; 514/195.1
See application file for complete search history.

(56) References Cited

U.S. PATENT DOCUMENTS

| 5,852,172 | A  | 12/1998 | Griffith |
| 5,972,679 | A  | 10/1999 | Griffith |
| 6,392,024 | B1 | 5/2002  | Graham et al. |
| 6,747,130 | B2 | 6/2004  | Graham et al. |
| 7,442,769 | B2 | 10/2008 | Hoshino et al. |
| 7,531,626 | B2 | 5/2009  | Graham et al. |
| 2002/0165383 | A1 | 11/2002 | Graham et al. |
| 2003/0022371 | A1 | 1/2003  | Griffith |
| 2003/0180884 | A1 | 9/2003  | Hoshino et al. |
| 2005/0019856 | A1 | 1/2005  | Tsuda et al. |
| 2006/0068470 | A1 | 3/2006  | Hoshino et al. |
| 2006/0116506 | A1 | 6/2006  | Graham et al. |

FOREIGN PATENT DOCUMENTS

| JP | 2002507889 A | 3/2002 |
| JP | 2004024237 A | 1/2004 |
| JP | 2004083546 A | 3/2004 |
| JP | 2004161761 A | 6/2004 |
| JP | 2004275008 A | 10/2004 |
| JP | 2005278638 A | 10/2005 |
| WO | 9222581 A1 | 12/1992 |
| WO | 9403617 A1 | 2/1994 |

OTHER PUBLICATIONS

Walters, Jr. et al, "A Nonprotein Thermal Hysteresis-Producing Xylomannan Antifreeze in the Freeze-Tolerant Alaskan Beetle *Upis ceramboides*", PNAS, vol. 106, No. 48, pp. 20210-20215 (Dec. 1, 2009).*
Machine Translation of Japanese Patent Specification No. JP 2004-275008 A (Oct. 2004).*
Kawahara, H., "Application in Food Industry and Function of Ice Crystal-controlling Materials Originated from Organisms", The Journal of Japanese Society for Cryobiology and Cryotechnology, vol. 55, No. 1/2, pp. 49-53, Oct. 31, 2009, 5 pages.
Yu, X. et al., "Antifreeze Proteins in Winter Rye Leaves Form Oligomeric Complexes", Plant Physiology, vol. 119, pp. 1361-1369, Apr. 2009, 9 pages.
Smallwood, M. et al., "Isolation and Characterization of a Novel Antifreeze Protein from Carrot (*Daucus carota*)", Biochemical Journal, vol. 340, pp. 385-391, Jun. 1999, 7 pages.
Puck, T. et al., "Genetics of Somatic Mammalian Cells", The Journal of Experimental Medicine, vol. 108, No. 6, pp. 945-956, Dec. 1, 1958, 12 pages.
ISA Japan, International Search Report of PCT/JP2011/068364, Sep. 9, 2011, WIPO, 2 pages.

* cited by examiner

*Primary Examiner* — Anthony J Green
(74) *Attorney, Agent, or Firm* — Alleman Hall McCoy Russell & Tuttle LLP

(57) ABSTRACT

The objective to be solved by the present invention is to provide an ice-crystallization inhibitor which has a practicable and excellent ice-crystallization inhibiting property and which can be efficiently and stably produced in a safe process suitable for food production. Also, the objective of the present invention is to provide an antibody which specifically reacts with the ice-crystallization inhibitor, and a composition, a food, a biological sample protectant and a cosmetic which contain the ice-crystallization inhibitor. Furthermore, the objective of the present invention is to provide a polysaccharide which is derived from a basidiomycete and which is used for inhibiting ice-crystallization of a liquid containing water, and a method for inhibiting ice-crystallization of a liquid containing water. The ice-crystallization inhibitor according to the present invention is characterized in being a polysaccharide derived from a basidiomycete.

4 Claims, No Drawings

ICE CRYSTALLIZATION INHIBITOR DERIVED FROM BASIDIOMYCETE

TECHNICAL FIELD

The present invention relates to an ice-crystallization inhibitor derived from a basidiomycete, an antibody which specifically responds to the ice-crystallization inhibitor, and a composition, a food, a biological sample protectant, and a cosmetic which contain the ice-crystallization inhibitor.

BACKGROUND ART

It is known that an organism that lives under low temperature conditions produces an ice-crystallization inhibitor such as an antifreeze protein and uses such an ice-crystallization inhibitor to protect its cells from freezing. Hereinafter, an antifreeze protein is referred to as "AFP". An AFP is a protein which exhibits characteristics such as thermal hysteresis, and can inhibit an aqueous solution from freezing by controlling the structures of ice-crystals. AFPs have been found in organisms such as a fish, an insect, a plant, a fungi and a microorganism.

In the past, AFPs have been found in fish such as a Cottidae, an insect such as a mealworm, a microorganism such as *Flavobacterium*, and the like, and the AFPs have a high activity for inhibiting ice-crystallization (Patent Documents 1 to 3). In addition, AFPs also have been found in a plant such as a winter rye and a carrot (Non-patent Documents 1 and 2).

Furthermore, AFPs derived from basidiomycete fungi such as *Typhula ishikariensis* and *Flammulina velutipes* KUAF-1 are known (Patent Documents 4 and 5).

Recently, there was an attempt at using AFPs for maintaining the quality of a frozen confection product and a frozen food, such as an ice cream, by industrially utilizing the above-described properties (Patent Documents 6 and 7).

PRIOR ART

Patent Document

Patent Document 1: JP2004-83546A
Patent Document 2: JP2002-507889T
Patent Document 3: JP2004-161761A
Patent Document 4: JP2004-24237A
Patent Document 5: JP2004-275008A
Patent Document 6: WO92/22581
Patent Document 7: WO94/03617

Non-Patent Document

Non-Patent Document 1: Plant Physiology, vol. 119, pp. 1361-1369 (1999)
Non-Patent Document 2: Biochem. J., vol. 340, pp. 385-391 (1999)

DISCLOSURE OF THE INVENTION

Problems to be Solved by the Invention

Regardless of the above-described properties, it is difficult to completely remove an odor from AFPs derived from a fish. In addition, AFPs derived from an insect and a microorganism are not suitable for foods, since it is difficult to use an insect and a microorganism as a raw material for foods.

On the other hand, AFPs derived from a plant can be used as a raw material for food, since plants are regularly used as raw materials for foods. However, AFPs derived from a plant have rarely been used industrially, since the binding ability thereof to an ice crystal is weaker than other AFPs and the AFPs derived from plants are not sufficiently stable against heat.

Accordingly, the objective to be solved by the present invention is to provide an ice-crystallization inhibitor which has a practicable and excellent ice-crystallization inhibiting property and which can be efficiently and stably produced in a safe process suitable for a food production. Also, the objective of the present invention is to provide an antibody which specifically reacts with the ice-crystallization inhibitor, and a composition, a food, a biological sample protectant, and a cosmetic which contain the ice-crystallization inhibitor. Furthermore, the objective of the present invention is to provide a polysaccharide which is derived from a basidiomycete and which is used for inhibiting ice-crystallization of a liquid containing water, and a method for inhibiting ice-crystallization of a liquid containing water.

Means for Solving the Problems

The present inventors have studied intensively to solve the above problems. As a result, the inventors have found an ice-crystallization inhibitor derived from a basidiomycete which exhibits a high activity for inhibiting ice-crystallization, to arrive at the present invention. The ice-crystallization inhibitor can be stably produced, is suitable for industrially application, and is not a protein.

The ice-crystallization inhibitor according to the present invention is a polysaccharide derived from a basidiomycete. The antibody according to the present invention is characterized in specifically responding with the ice-crystallization inhibitor according to the present invention.

The composition, food, biological sample protectant, and cosmetic according to the present invention are characterized in comprising the ice-crystallization inhibitor according to the present invention.

The polysaccharide derived from a basidiomycete according to the present invention is used for inhibiting ice-crystallization of a liquid containing water. The method for inhibiting ice-crystallization of a liquid containing water according to the present invention is characterized in comprising the step of adding a polysaccharide derived from a basidiomycete to the liquid.

For example, the polysaccharide contains mannose and xylose, or galactose, mannose, xylose, glucose, rhamnose or a combination of two or more selected therefrom. More specifically, the polysaccharide is exemplified by xylomannan. With respect to xylomannan containing xylose and mannose, it is exemplified that a constituent ratio of the mannose relative to 1 mole of the xylose is not less than 1.5 and not more than 2.5 in the xylomannan, or a molecular weight of the xylomannan is not less than 280,000 and not more than 340,000.

The basidiomycete which produces the ice-crystallization inhibitor according the present invention is exemplified by *Flammulina velutipes*, *Lyophyllum decastes*, *Pleurotus eryngii*, *Lyophyllum shimeji*, *Pholiota nameko*, an allied species thereof and an improved species thereof, and is particularly exemplified by *Flammulina velutipes*, an allied species thereof and an improved species thereof.

Effect of the Invention

The ice-crystallization inhibitor according to the present invention is harmless to a living body, since the inhibitor contains a polysaccharide and can be easily obtained from a basidiomycete which is suitable for eating. In addition, the inhibitor of the present invention can be stably supplied, since the inhibitor is derived from a basidiomycete. Furthermore, the inhibitor of the present invention has an excellent ice-crystallization inhibiting activity at a practical level.

MODE FOR CARRYING OUT THE INVENTION

The ice-crystallization inhibitor according to the present invention is a polysaccharide derived from a basidiomycete.

The ice-crystallization inhibitor according to the present invention is a polysaccharide which has a function to inhibit the growth of an ice crystal by, for example, binding to the crystal surface thereof. Such a polysaccharide has an ice-crystallization inhibiting activity which can be confirmed by any one of publicly known methods such as measuring a thermal hysteresis, observation of ice crystal structures, and measurement of ice-crystal growth inhibiting characteristics.

A thermal hysteresis is exhibited over a temperature range which is less than the equilibrium melting point of the aqueous solution containing an ice-crystallization inhibiting activity but in which ice crystals cannot grow, and is detected as a difference between the equilibrium melting point and the freezing point, whereinthe freezing point is defined as a temperature at which ice crystals start to grow in the aqueous solution.

The ice-crystallization inhibitor according to the present invention is a polysaccharide. A polysaccharide usually means a polymer in which ten or more monosaccharides are bonded with glycosidic bonds linearly or in a branched manner.

A polysaccharide is classified as a homopolysaccharide or a heteropolysaccharide. A homopolysaccharide is a simple polysaccharide consisting of one kind of monosaccharide, and a heteropolysaccharide is a complex polysaccharide consisting of two or more kinds of monosaccharides. A homopolysaccharide is exemplified by a starch such as amylose and amylopectin; glycogen; cellulose; glucan; xylan; and mannan. A heteropolysaccharide is exemplified by hyaluronic acid, heparin, xylomannan, xyloglucan and glucomannan.

The polysaccharide derived from a basidiomycete according to the present invention is not particularly limited, and is exemplified by a polysaccharide containing mannose and xylose, and a polysaccharide consisting of galactose, mannose, xylose, glucose, rhamnose, or two or more thereof. The polysaccharide derived from a basidiomycete according to the present invention is preferably a heteropolysaccharide, and more preferably xylomannan. Xylomannan is a generic name of a heteropolysaccharide in which side chains consisting of one molecule of xylose bind to a main mannan chain consisting of α-1,3-mannose molecules bonded through a 1,4-linkage. However, in the present invention, the xylomannan is not limited to a molecule consisting of mannose and xylose only, and may have sugars other than xylose as side chains.

In the present invention, the constituent ratio of mannose and xylose in a xylomannan is not particularly limited. For example, the ratio of mannose relative to 1 mole of xylose is preferably not less than 1.5, not more than 2.5, more preferably not less than 1.7, not more than 2.3, even more preferably not less than 1.9, not more than 2.1, and particularly preferably about 2.

The molecular weight of the ice-crystallization inhibitor according to the present invention is not particularly limited. For example, the average molecular weight measured with gel filtration chromatography is preferably not less than 100,000, and not more than 1,000,000. The average molecular weight is more preferably not less than 150,000, even more preferably not less than 200,000, even more preferably not less than 240,000, particularly preferably not less than 280,000, and more preferably not more than 500,000, even more preferably not more than 400,000, even more preferably not more than 370,000, and particularly preferably not more than 340,000.

The ice-crystallization inhibitor according to the present invention is derived from a basidiomycete, and can be produced from a basidiomycete. Hereinafter, a method for producing the ice-crystallization inhibitor according to the present invention is described.

(1) Culturing Step

The ice-crystallization inhibitor according to the present invention may be produced from a commercially available basidiomycete or a harvested basidiomycete. In particular, when the ice-crystallization inhibitor is industrially produced in a large volume, it is more efficient to culture a basidiomycete. In other words, when the ice-crystallization inhibitor is produced, a basidiomycete may be arbitrarily cultured.

A basidiomycete for producing the ice-crystallization inhibitor according to the present invention is exemplified a basidiomycete belonging to the order Agaricales. A basidiomycete belonging to the order Agaricales is exemplified by basidiomycetes belonging to the family Hygrophoracea, family Tricholomataceae, family Amanitaceae, family Agaricaceae, family Coprinaceae, family Strophariaceae, family Cortinariaceae, family Boletaceae, family Russulaceae, family Polyporaceae and family Pleurotaceae.

A basidiomycete belonging to the family Hygrophoracea is exemplified by *Hygrophorus camarophyllus* and the like. A basidiomycete belonging to the family Tricholomataceae is exemplified by *Tricholoma equestre, Lepista nuda, Lyophyllumconnatum, Lyophyllum sykosporum, Lyophyllum fumosum* (Fr.) Orton, *Entoloma clypeatum* (L.) Kummer, *Lyophyllum decastes* (Fr.) Singer, *Hypsizygus marmoreus, Lyophyllum shimeji, Marasumius maximus* Hongo, *Pleurocybella porrigens, Marasmius siccus, Laccaria laccata, Armillaria mellea* (Vahl:Fr.) Kummer, *Panellus serotinus* (Fr.) Kühner, *Tricholoma matsutake* (S. Ito et Imai) Sing., *Tricholoma radicans* Hongo, *Lentinus edodes* (Berk.) Sing., *Flammulina velutipes* (Curt.: Fr.) Sing. and the like. A basidiomycete belonging to family Amanitaceae is exemplified by *Amanita hemibapha* (B. et Br.) Sacc., *Amanita vaginata* (Bull.: Fr.) Vitt. var. *fulva* (Schaeff.) Gill. and the like. A basidiomycete belonging to family Agaricaceae is exemplified by *Agaricus campestris, Agaricus arvensis* and the like. A basidiomycete belonging to family Coprinaceae is exemplified by *Coprinus atramentarius* (Fr.) Fr. and the like. A basidiomycete belonging to family Strophariaceae is exemplified by *Pholiota nameko* and the like. A basidiomycete belonging to family Cortinariaceae is exemplified by *Rozites caperata* (Fr.) Karst. and the like. A basidiomycete belonging to family Boletaceae is exemplified by *Boletus edulis* Fr. and the like. A basidiomycete belonging to family Russulaceae is exemplified by *Russula virescens* Fr. and the like. A basidiomycete belonging to family Polyporaceae is exemplified by *Grifola frondosa* (Fr.) S. F. Gray and the like. A basidiomycete belonging to family Pleurotaceae is exemplified by *Pleurotus eryngii* and the like.

The ice-crystallization inhibitor according to the present invention is not particularly limited, and for example, can be preferably obtained from *Flammulina velutipes, Lyophyllum*

*decastes, Pleurotus eryngii, Lyophyllum shimeji* and *Pholiota nameko*, and more preferably obtained from *Flammulina velutipes*.

Among the above-described *Flammulina velutipes*, a commercially available white *Flammulina velutipes* which is cultivated by an artificial method and which is in the form of a sprout is preferred, since such a commercially available *Flammulina velutipes* is generally used as a food and easily available. In addition, the extract obtained from the *Flammulina velutipes* has an excellent ice-crystallization inhibiting activity per unit weight of the basidiomycete.

The allied species and improved species of the above basidiomycetes can be arbitrarily used.

With respect to the term "allied species" in the present invention, as an example, an allied species of a family may include a breed variety which belongs to the same genus but is different from and close to the basidiomycete to be compared in scientific classification, and an allied species of a specific basidiomycete may include a breed variety which belongs to the same family but is different from and close to the basidiomycete to be compared in scientific classification. The term "improved species" may include a specific basidiomycete improved by artificial selection, hybridization, mutation, gene recombination and the like.

The method for culturing the basidiomycete used in the present invention is not particularly limited, and the basidiomycete can be cultured with a conventional method such as a solid culture method and a liquid culture method. For example, in a solid culture method, a mycelium is inoculated on a solid medium containing a plant fiber material such as bagasse, wheat bran and rice bran for cultivation to obtain a mycelium or a fruit body. In a liquid culture method, a mycelium is inoculated into a medium containing a carbon source, a nitrogen source, a mineral, and other necessary nutrients to be utilized by the strain, and in a conventional cultivation such as a shake culture, an aeration-stirring culture and static culture may be carried out.

The culture conditions such as culture temperature and culture time may be properly adjusted, and it is preferred to culture at a low temperature. The ice-crystallization inhibitor can be induced by culturing a basidiomycete at a relatively low temperature, in other words, by acclimatizing a basidiomycete to low temperature. The culture temperature is, for example, preferably not more than 25° C., and more preferably not more than 20° C. On the other hand, the culture temperature is preferably not less than 0° C., since a liquid medium may be possibly frozen below the freezing point.

The culture time is not particularly limited, and is preferably set to be not less than 3 days, more preferably not less than 1 week, even more preferably not less than 2 weeks, and particularly preferably not less than 1 month. The upper limit of the culture time is also not limited, and a basidiomycete may be cultured confluently or until a concentration of the ice-crystallization inhibitor in the culture medium no longer increases. For example, the culture time is preferably not more than 6 months, more preferably not more than 5 months, even more preferably not more than 4 months, and particularly preferably not more than 3 months.

(2) Extraction Step The ice-crystallization inhibitor according to the present invention can be obtained from a basidiomycete by extraction. For example, the ice-crystallization inhibitor can be extracted from the above-described basidiomycete with heating treatment in an alkaline aqueous solution.

The portion of the basidiomycete used in the present invention is not limited, and for example, any of a mycelium and a fruit body can be used. In the present invention, only one portion may be used and two or more portions may be used in combination.

The form of the basidiomycete used for extracting the ice-crystallization inhibitor according to the present invention may be in the raw, crushed form, grinded form, dried form or dried and crushed form. As the basidiomycete in the raw, a mycelium separated from a mycelium culture obtained by the above-described culture method and a mycelium culture itself may be used.

The ice-crystallization inhibitor according to the present invention may be obtained by adding an alkaline aqueous solution to a basidiomycete which may be arbitrarily treated as above, and heating the mixture for extraction.

An alkali substance used for preparing the alkaline aqueous solution is exemplified by sodium hydroxide, potassium hydroxide, calcium hydroxide, sodium carbonate, sodium polyphosphate, trisodium citrate, sodium bicarbonate, sodium acetate, sodium pyrophosphate, disodium hydrogenphosphate, dipotassium hydrogenphosphate, trisodium phosphate, tripotassium phosphate and calcium obtained by calcination. One of such an alkali substance may be used singly, and two or more may be used in combination.

The concentration of the alkaline aqueous solution may be properly adjusted depending on the kind of the polysaccharide and the like, and for example, is preferably not less than 0.1 w/v %, more preferably not less than 1.0 w/v %, more preferably not less than 2.0 w/v %, more preferably not less than 5.0 w/v %, more preferably not less than 10.0 w/v %, more preferably not less than 15.0 w/v %, particularly preferably not less than 20.0 w/v %, and preferably not more than 50 w/v %, more preferably not more than 30 w/v %, more preferably not more than 25 w/v %. When the concentration is less than 0.1 w/v %, the extraction efficiency of the objective ice-crystallization inhibitor may be insufficient; and when the concentration is more than 50 w/v %, there may be a problem with cost and safety.

The temperature of the heating-extraction treatment is preferably not less than 70° C., more preferably not less than 80° C., even more preferably not less than 90° C., and most preferably about 100° C. As the heating-extraction treatment method, for example, the mixture of a basidiomycete and an alkaline aqueous solution may be heated up to the predetermined temperature for extraction, or an alkaline aqueous solution which is preliminarily heated up to the predetermined temperature may be added to a basidiomycete and the temperature may be maintained for extraction.

More specifically, a 25 w/v % potassium hydroxide aqueous solution is added to a dried and crushed basidiomycete, and the mixture is heated at 100° C. for 2 to 3 hours for extraction, and the extract is obtained by filtration or centrifugation. The extract can be used as the ice-crystallization inhibitor. Further, a similar extraction treatment is repeated for the extraction residue, and obtained extracts are combined to be used as the ice-crystallization inhibitor.

(3) Purification Step

The extract obtained by the above-described step may be directly used. Alternatively, a liquid product obtained by removing the alkali substance using a well-known method such as neutralization and dialysis, the concentrate thereof, the dried product thereof and the dried and crushed product thereof are preferably used as the ice-crystallization inhibitor.

The ice-crystallization inhibitor obtained as described above may be further purified as necessary. For example, a contaminating substance may be removed by a preferable combination of decantation, filtration, centrifugation and the like. In addition, for example, precipitation by salting-out or using an organic solvent, affinity chromatography, ion-exchange column chromatography, gel filtration, purification by binding to ice using a low-speed refrigerator, concentration by dialysis or ultrafiltration, and the like may be properly combined.

(4) Formulation Step

As necessary, the ice-crystallization inhibitor according to the present invention may be further formed into an arbitrary form such as a powder and a granule. A method of formulation is not particularly limited, and is exemplified by a method for powderizing the above extract with a conventional method such as spray drying and freeze drying, a method for powderizing or granulating the extract by adsorbing and supporting the extract on an excipient, and the like. Such methods are well-known for the person skilled in the art, and the skilled person can select an appropriate method to be used depending on the intended use application.

The ice-crystallization inhibitor according to the present invention binds to the crystal surface of an ice crystal and inhibits the growth of the ice crystal. In addition, such a binding inhibits the recrystallization of ice by blocking free water from further binding to the ice crystal.

The ice-crystallization inhibiting activity of the ice-crystallization inhibitor according to the present invention is measured with an appropriate method depending on the kind of the inhibiting activity to be measured, the kind of the basidiomycete to be used, and the like. For example, the activity can be confirmed with a publicly known method such as measurement of a thermal hysteresis, observation of the ice crystal structures, and measurement of ice-crystal growth inhibiting characteristics. The ice-crystallization inhibitor which shows an ice-crystallization inhibiting activity demonstrated by any one of known methods is included in the range of the present invention.

For example, the ice-crystallization inhibiting activity can be measured by cooling an ice-crystallization inhibitor aqueous solution containing 30 w/v % sucrose down to −40° C., then raising the temperature up to −6° C., and measuring an average area of ice crystals observed by a microscope. As a control, an average area of ice crystals in a 30 w/v % sucrose aqueous solution is similarly measured. Since the average area of ice crystals is smaller as the ice-crystallization inhibiting activity is stronger, the ice-crystallization inhibiting activity of the ice-crystallization inhibitor can be quantitatively evaluated using the value obtained by dividing the measured average value by the control average value as an index. The calculated value is referred to as RI value. For example, when the addition of the ice-crystallization inhibitor leads to the inhibition of the growth of ice crystals as compared with a control, the inhibitor is considered as having an ice-crystallization inhibiting activity.

The ice-crystallization inhibitor according to the present invention can be utilized in various fields for preventing problems caused by crystallization of water. For example, the inhibitor can be utilized in fields of such as the food industry, machinery, civil engineering, cosmetics, and medicine, in which a biological sample is used.

In the food industry, it is possible to prevent the deterioration of taste and other properties by suppressing ice-crystallization of water contained in a food. For example, it is possible to prevent starch from aging. In addition, when water in a food is crystallized to ice, the protein, fat components, oil components, and the like are physically compressed, and the structure of the components is changed. As a result, taste, quality and the like of a food is deteriorated. When the ice-crystallization inhibitor is added to a food, such deterioration can be inhibited and the quality of a frozen food and the like can be improved.

In the fields of machinery and civil engineering, the ice-crystallization inhibitor according to the present invention can be utilized as a cryoprotective agent for movable parts of machinery, roads, the ground, and the like.

In the field of cosmetics, the ice-crystallization inhibitor according to the present invention can be utilized as an additive agent for preventing the reduction in quality of cosmetics. For example, when cosmetics containing an oil component or a fat component are frozen, water contained in the cosmetics is crystallized to ice. As a result, the oil component and fat component may be physically compressed and the structure thereof may be destroyed, whereby the quality and usability of the cosmetics become deteriorated. When the ice-crystallization inhibitor according to the present invention is used, the reduction in quality and the like can be avoided since ice-crystallization of water is prevented and the structure of an oil component and a fat component is maintained.

In the field of medicine, the ice-crystallization inhibitor according to the present invention can be utilized as a protectant when a biological sample is cryopreserved. When a biological sample such as a cell, blood and an organ is cryopreserved in a conventionally and publicly known preservation solution, water in the preservation solution freezes and generates ice crystals. The ice crystals may damage the biological sample. On the other hand, when the ice-crystallization inhibitor according to the present invention is added thereto, the biological sample can be protected from the damage caused by ice crystals since generation and growth of ice crystals can be suppressed.

The ice-crystallization inhibitor of the present invention may have various forms depending on the application thereof. The ice-crystallization inhibitor may be used as is, or may be used in the form of a solution, a concentrated solution, a suspension, a freeze-dried product, a powder, a granule, a tablet and the like. In addition, the ice-crystallization inhibitor may be mixed with an excipient to be used as a composite substance.

The antibody according to the present invention reacts specifically with the above-described ice-crystallization inhibitor and binds to the inhibitor. The antibody therefore can be used for confirming the presence or absence of the ice-crystallization inhibitor in a basidiomycete or the culture medium therefor, and specifying a polysaccharide having an ice-crystallization inhibiting activity from a culture medium for a basidiomycete.

The antibody according to the present invention may be produced according to a conventional method. For example, a mouse, rat or the like is immunized with the above-described ice-crystallization inhibitor, and the antibody-producing cell or the splenocyte is fused with a myeloma cell to obtain a hybridoma. The hybridoma is cloned, and the clone producing an antibody which is reactive specifically with the above-described ice-crystallization inhibitor is screened. The clone is cultured, and a secreted monoclonal antibody may be purified.

As described above, the polysaccharide derived from a basidiomycete according to the present invention can be used for inhibiting the ice-crystallization of a liquid which contains water. The method for inhibiting ice-crystallization of a liquid containing water according to the present invention is characterized in comprising the step of adding a polysaccharide derived from a basidiomycete into the liquid.

The liquid in which ice-crystallization is inhibited by the present invention is not particularly limited as long as the liquid contains water as a solvent. The liquid is exemplified by water itself, an aqueous solution in which a solute is dissolved, and a dispersion in which an insoluble component is dispersed. In addition, the liquid in which ice-crystallization is inhibited may contain a water-miscible organic solvent as long as the ice-crystallization thereof is problematic. Such a water-miscible organic solvent is exemplified by an alcohol such as ethanol and a glycol such as ethylene glycol.

When ice-crystallization of a liquid is inhibited by the polysaccharide derived from a basidiomycete according to the present invention, an additive amount of the polysaccharide may be properly adjusted depending on the concentration of the solute contained in the liquid and the solidification point of the liquid, and may be adjusted to be not less than about 0.05 µg/ml and not more than about mg/ml on the saccharide concentration basis. When the concentration is not less than 0.05 µg/ml, the ice-crystallization of a liquid can be more certainly inhibited. On the other hand, the concentration is preferably not more than 10 mg/ml, since when the concentration is too high, the ice-crystallization inhibiting effect may not be further increased in some cases in proportion with such a high concentration. The concentration is more preferably not less than 0.1 µg/ml, even more preferably not less than 0.5 µg/ml, and more preferably not more than 1 mg/ml, even more preferably not more than 400 µg/ml, particularly preferably not more than 200 µg/ml.

The present invention method includes the case where the polysaccharide of the present invention is implicitly added to a liquid in which ice-crystallization should be inhibited as well as the case where the present invention polysaccharide is explicitly added to a liquid of which ice-crystallization should be inhibited. For example, the present invention includes the case where the present invention polysaccharide is spread on a road and the like, the polysaccharide is dissolved by contact with night dew, and freezing of the road is inhibited.

EXAMPLES

Hereinafter, the present invention is specifically described in more detail with Examples. The present invention is not limited to the following Examples in any way.

Example 1

100 ml of YG culture medium (containing 0.25% yeast extract and 1% glucose, pH 6.0) was added to a 500 ml-volume conical flask, and a hypha of a commercially available *Flammulina velutipes* was inoculated. A rotary culture was carried out at 120 rpm and 18° C. for one week, and a low temperature-acclimation (habituation) culture was further carried out at 4° C. for one week.

The hypha of *Flammulina velutipes* after the low temperature-temperature-acclimation (habituation) was washed and then freeze-dried. Water (500 ml) was added to the freeze-dried *Flammulina velutipes* (50 g), and the mixture was heated at 100° C. for 6 hours. Then, the solid contents were separated by filtration. The obtained residue was similarly treated by hot water three times, and the residue (34.4 g) was recovered.

Next, a 2 w/v % potassium hydroxide aqueous solution (500 ml) was added to the above residue (34.4 g) after the hot water-treatment, and the mixture was heated at 100° C. for 2.5 hours. Hereinafter, such a treatment is referred to as "2% KOH treatment". The solid contents were separated by filtration, and a similar 2% KOH treatment was repeated three times for the obtained residue. A 25 w/v % potassium hydroxide aqueous solution (500 ml) was added to the obtained residue, and the mixture was heated at 100° C. for 2.5 hours. Hereinafter, such a treatment is referred to as "25% KOH treatment". A similar 25% KOH treatment was repeated three times for the treated residue. The above extracts were recovered and mixed.

The obtained solution was concentrated using an evaporator. 3 times the volume of ethanol was added to the concentrated solution. The sediment precipitated by adding ethanol was dispersed into water. The dispersion was neutralized using an acetic acid aqueous solution and then dialyzed using water for 48 hours. The dispersion was frozen, and then slowly melted at 4° C. The precipitated sediment was separated by centrifugation to be recovered.

The obtained sediment was dissolved into dimethylsulfoxide (DMSO), and the solution was heated at 40° C. for 48 hours. Then, the supernatant was recovered and freeze-dried to remove DMSO. As a result, a xylomannan fraction (0.164 g) was obtained. The obtained xylomannan fraction was dissolved in water (46 ml). The concentrations of sugars and proteins were respectively measured with phenol-sulfuric acid method and bicinchoninic acid assay method (BCA method). The concentrations were 6.3 µg/ml and 4.4 µg/ml, respectively.

Example 2

The aqueous solution of the xylomannan obtained in Example 1 was diluted so that the sugar concentration became 1.0 µg/ml and the protein concentration became 0.7 µg/ml, and the ice-crystallization inhibiting activity was measured. Specifically, first, sucrose was added to the diluted solution at a concentration of 30 w/v %. Under a microscope having a stage with cooling control function, the solution was cooled down to −40° C., and then the temperature was raised up to −6° C. to melt ice crystals. In the state of keeping −6° C., the ice-crystallization inhibiting activity was measured by measuring the areas of the ice crystals observed with the microscope after 30 minutes. As a control, the same measurement was carried out for a 30 w/v % sucrose solution. A smaller average area of ice crystals shows stronger ice-crystallization inhibiting activity. Therefore, the measured average area was divided by the control average area. An ice-crystallization inhibiting activity was quantitatively assessed using the calculated value as the indicator. The calculated value is referred to as "RI value". The RI value was 0.25. A smaller RI value of less than 1.0 shows stronger ice-crystallization inhibiting activity.

Example 3

A xylomannan fraction (1.5 mg) was purified by a similar method as Example 1 except that 0.46 g of dried hypha of *Flammulina velutipes* was used. The obtained xylomannan fraction was dissolved in a 50 mM phosphate buffer solution (pH 7.0) containing 0.3 M sodium chloride. The obtained aqueous solution (200 µl, sugar concentration: 3.9 mg/ml, protein concentration: 17 µg/ml) was used as a sample for a gel filtration column (manufactured by TOSOH Corporation, TSK-gel G3000SW$_{XL}$, 21.5 mm I.D.×30 cm), and the non-adsorptive fraction was eluted using the above-described phosphate buffer solution at 4° C. at a flow velocity of 2.0 ml/min. Detection was carried out by absorption wavelengths of 215 nm and 280 nm.

In the non-adsorptive fraction in the gel filtration chromatography, a single peak was observed at a molecular weight of about 310,000. The fraction was recovered, and the ice-crystallization inhibiting activity was measured using the same method as Example 2.

Example 4

The purified sample obtained in Example 3 was dissolved in a 0.2 M potassium borate buffer solution (pH 8.9) containing 7 v/v % of acetonitrile. The obtained aqueous solution (50 μl, 1.0 μg of purified sample) was used as a sample for a column for analyzing sugar composition (manufactured by SEIKAGAKU Corporation, Honenpak C18, 21.5 mm I.D.× 30 cm), and the non-adsorptive fraction was eluted using the above-described potassium borate buffer solution as an eluent at 30° C. and a flow velocity of 1.0 ml/min. Detection was carried out using an excitation wavelength of 305 nm and fluorescence wavelength of 360 nm. In addition, mannose, glucose and xylose (respectively 1.5 nmol) were eluted as standard substances under the same condition. It was confirmed by the retention time and fluorescence intensity of the observed peak that the sugar composition of the purified sample contained mannose:xylose in a 2:1 molar ratio.

Example 5

A fruit body of a commercially available *Lyophyllum decastes* was freeze-dried. A 15 w/v % potassium hydroxide aqueous solution (10 ml) was added to the obtained freeze-dried *Lyophyllum decastes* fruit body (0.2 g), and the mixture was heated at 100° C. for 2.5 hours. Then, the mixture was centrifuged at 10,000×g for 20 minutes to obtain a crude solution.

The crude solution obtained by a similar method to Example was treated with ethanol, and the precipitated sediment was recovered. The obtained precipitation was dissolved in a 20 mM Tris-HCl buffer solution (pH 8.0). The resultant solution is referred to as an ethanol recover fraction.

Example 6

An ethanol recover fraction was obtained from a commercially available fruit body of *Pleurotus eryngii* by a method similar to Example 5.

Example 7

An ethanol recover fraction was obtained from a commercially available fruit body of *Lyophyllum shimeji* by a method similar to Example 5.

Example 8

An ethanol recover fraction was obtained from a commercially available fruit body of *Pholiota nameko by a method similar to Example 5.*

Example 9

The ethanol recover fractions which were obtained in Examples 5 to 8 and which were derived from basidiomycetes were diluted with water so that the sugar concentrations respectively became 1.0 μg/ml, and the ice-crystallization inhibiting activities thereof were measured with the same method as Example 2. The results are shown in Table 1.

TABLE 1

|  | Example 5 | Example 6 | Example 7 | Example 8 |
| --- | --- | --- | --- | --- |
| Ice-crystallization inhibiting activity (RI value) | 0.36 | 0.55 | 0.59 | 0.64 |

Example 10

The ethanol recover fraction from *Lyophyllum decastes* obtained in Example 5 was fractionated by a gel filtration chromatography using the same method as Example 3, and the fraction showing the molecular weight peak of about 467,000 was obtained. The sugar concentration of the obtained fraction was adjusted to be 5.0 mg/ml, and the ice crystallization inhibiting activity was measured with the same method as Example 2. As a result, RI value was 0.29.

Example 11

The sugar composition of the purified sample obtained in Example 10 was analyzed with the same method as Example 4. As a result, it was confirmed by the retention time of the observed peak that the purified sample was a polysaccharide consisting of galactose, mannose, xylose, glucose and rhamnose.

Example 12

A hypha of a *Flammulina velutipes* was freeze-dried with a similar method as Example 1. The obtained freeze-dried *Flammulina velutipes* hypha (20.0 g) was treated with hot water three times, and then a 2.0 w/v % potassium hydroxide aqueous solution (200 ml) was added thereto. The mixture was heated at 100° C. for 2.5 hours. Then, the mixture was centrifuged at 10,000×g for 20 minutes to obtain a crude extract solution. The obtained crude extract solution was freeze-dried to obtain a crude xylomannan fraction (2.05 g).

Example 13

Frozen octopus dumpling

An aqueous solution of the crude xylomannan fraction obtained in Example 12 was mixed with a commercially available octopus dumpling mix of the composition shown in Table 2, and the mixture was cooked using a household octopus dumpling cooker to obtain octopus dumplings. The obtained octopus dumplings were frozen at −20° C. using a quick cooler for professional use. For comparison, octopus dumplings were prepared and frozen in the same manner except that the crude xylomannan fraction was not used. The concentrations of the crude xylomannan fractions were respectively 10 μg/ml and 50 μg/ml on a sugar concentration basis.

TABLE 2

| Octopus dumpling mix | 70 g | 70 g | 70 g |
| --- | --- | --- | --- |
| Water | 200 ml | 200 ml | 200 ml |
| Crude xylomannan fraction (protein conversion) | 2 mg | 10 mg | — |

The obtained frozen octopus dumplings were preserved for 1 week and then thawed at ambient temperature. The thawed octopus dumplings were cut in half, and the cut surface was observed. The octopus dumplings which did not contain the crude xylomannan fraction dropped in quality due to freezing and thawing, the octopus dumplings forming a gap between the surface and inside thereof. On the other hand, such a gap did not form between the surface and the inside of the octopus dumplings which contained the crude xylomannan fraction, the condition before freezing being maintained after thawing. The result demonstrates that even if a food is frozen, the quality of the food can be maintained by using the ice-crystallization inhibitor according to the present invention.

Example 14

Frozen steamed egg yolk

The crude xylomannan fraction obtained in Example 12 was mixed with an egg yolk. At the time, the amount of the crude xylomannan fraction was adjusted so that the sugar concentration of the mixture became 50 µg/ml. The obtained egg yolk mixture was steamed using a water oven (manufactured by Sharp Corporation, Healsio AX-MX1-R) for 15 minutes to obtain a steamed egg yolk. Then, the obtained steamed egg yolk was frozen at -20° C. using a quick freezer for professional use. For comparison, a similar steamed egg yolk was prepared and frozen except that a crude xylomannan fraction was not used.

Each steamed egg yolk was preserved for one week, and then thawed at ambient temperature. After thawing, the appearance and texture thereof were compared. The steamed egg yolk which did not contain the crude xylomannan fraction had a rough surface due to freezing and thawing, and the texture thereof became very mealy. On the other hand, in the case where the crude xylomannan fraction was added, the condition of the steamed egg yolk before freezing was maintained as the steamed egg yolk had a fine surface and the texture thereof was resilient and fresh. Accordingly, it was experimentally demonstrated that even when a food is frozen, the quality thereof can be maintained by using the ice-crystallization inhibitor according to the present invention.

Example 15

Protection of frozen cell

A Chinese hamster ovary cell (CHO cell) was continuously cultivated according to a general method described in Theodore T. PUCK et al., The Journal of Experimental Medicine, vol. 108, pp. 945- (1958), and then detached with trypsin treatment and recovered with centrifugation. A medium was added to the recovered cell, and the mixture was centrifuged again to remove trypsin. The obtained cell was dispersed into a cryopreservation medium ("Cell bunker" manufactured by Nippon Zenyaku Kogyo Co., Ltd.). The purified xylomannan fraction obtained by a similar method described in Example 1 was added to the dispersion, and the mixture was sufficiently mixed using a pipette. The concentration of the purified xylomannan fraction in the dispersion was adjusted to be 20 µg/ml, 50 µg/ml and 200 µg/ml on the basis of sugar concentration. The obtained cell dispersion was dispensed in increments of 1 ml into cryogenic vials and frozen at -80° C. using a deep freezer.

In addition, for comparison, the CHO cell which was recovered similarly to the above was dispersed into a 10 v/v % DMSO solution, and the mixture was sufficiently mixed using a pipette. Then, the obtained cell dispersion was dispensed in increments of 1 ml into cryogenic vials and frozen at -80° C. using a deep freezer.

Furthermore, for comparison, the CHO cell which was recovered similarly to the above was dispersed into a cryopreservation medium ("Cell bunker" manufactured by Nippon Zenyaku Kogyo Co., Ltd.) which did not contain xylomannan, and the mixture was sufficiently mixed using a pipette. Then, the obtained cell dispersion was dispensed in increments of 1 ml into cryogenic vials and frozen at -80° C. using a deep freezer.

The cryopreservation media which were prepared as the above were preserved in a frozen state in a freezer for 2 days. Then, the cryogenic vials were taken out from the freezer, and thaw was immediately carried out by immersing the cryogenic vials into a water bath of 37° C. After the thaw, the cell was immediately dispersed into a medium (10 ml), and centrifugation was carried out. The recovered cell was dispersed into a medium (1 ml) again. The dead cells in the obtained cell dispersion were selectively stained by Trypan Blue. The numbers of live cell and dead cell were counted using an erythrocytemeter, and the survival rate of cell was calculated. The result is shown in Table 3.

TABLE 3

| Xylomannan fraction concentration (µg/ml) | 20 | 50 | 200 | 0 (DMSO solution only) | 0 (cell culture freezing medium only) |
|---|---|---|---|---|---|
| Cell survival rate (%) | 97.2 | 96.6 | 98.4 | 13.5 | 83.2 |

As shown in Table 3, about 85% of the cells dispersed in a DMSO solution died due to freezing. It is said that a cell can be cryopreserved over a long period of time by using a cryopreservation media. In the case of using a cryopreservation media, cell survival rate was increased as compared to the cryopreservation with DMSO solution but only increased to 83.2%. On the other hand, when a xylomannan fraction, the ice-crystallization inhibitor according to the present invention, was added to a cryopreservation media, the cell survival rate was remarkably increased to about 100%. Thus, it was experimentally demonstrated from the above result that the ice-crystallization inhibitor according to the present invention is very useful as a biological sample protectant.

Industrial Applicability

When the ice-crystallization inhibitor according to the present invention is added to a food, the quality of the food can be maintained. In addition, the ice-crystallization inhibitor according to the present invention is useful as a cryoprotectant for cryopreserving biological samples such as an organ, a cell, blood platelets, and as a cosmetic which can protect skin from low temperatures and which has properties such as excellent low-temperature stability.

The invention claimed is:

1. A method for inhibiting ice-crystallization of a liquid containing water, comprising the step of adding a xylomannan derived from a basidiomycete to the liquid,
   wherein the xylomannan contains mannose and xylose, and a constituent ratio of the mannose relative to 1 mole of the xylose is not less than 1.5 moles and not more than 2.5 moles in the xylomannan, and
   the xylomannan is produced by a process comprising extraction of the xylomannan from the basidiomycete with heating treatment in an alkaline aqueous solution.

2. The method according to claim 1, wherein a molecular weight of the xylomannan is not less than 280,000 Da and not more than 340,000 Da.

3. The method according to claim 1, wherein the basidiomycete is Flammulina velutipes, Lyophyllum decastes, Pleurotus eryngii, Lyophyllum shimeji, Pholiota nameko, an allied species thereof or an improved species thereof, wherein
the allied species thereof comprises a basidiomycete belonging to the same family as the basidiomycete, and
the improved species thereof comprises the basidiomycete improved by at least one or more of artificial selection, hybridization, mutation, and gene recombination.

4. The method according to claim 1, wherein the basidiomycete is Flammulina velutipes, an allied species thereof or an improved species thereof, wherein
the allied species thereof comprises a basidiomycete belonging to the same family as the basidiomycete, and
the improved species thereof comprises the basidiomycete improved by at least one or more of artificial selection, hybridization, mutation, and gene recombination.

\* \* \* \* \*